US012714875B2

(12) United States Patent
Yamashita

(10) Patent No.: US 12,714,875 B2
(45) Date of Patent: Aug. 25, 2026

(54) PHOTOTHERAPY PROGRESS MEASURING METHOD, PROCESSOR, AND PHOTOTHERAPY SYSTEM

(71) Applicant: OLYMPUS CORPORATION, Tokyo (JP)

(72) Inventor: Susumu Yamashita, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 383 days.

(21) Appl. No.: 18/379,050

(22) Filed: Oct. 11, 2023

(65) Prior Publication Data

US 2024/0033535 A1 Feb. 1, 2024

Related U.S. Application Data

(63) Continuation of application No. PCT/JP2021/017216, filed on Apr. 30, 2021.

(51) Int. Cl.
*A61N 5/06* (2006.01)

(52) U.S. Cl.
CPC ........ *A61N 5/06* (2013.01); *A61N 2005/0628* (2013.01)

(58) Field of Classification Search
CPC .............. A61N 5/06; A61N 2005/0628; A61N 2005/0626; A61B 5/0071
See application file for complete search history.

(56) References Cited

U.S. PATENT DOCUMENTS 6,128,525 A 10/2000 Zeng et al.
6,238,426 B1 5/2001 Chen
2009/0099459 A1 4/2009 Svanberg et al.
2009/0303319 A1 12/2009 Sato et al.
2011/0118547 A1 5/2011 Erikawa
2013/0123642 A1 5/2013 Yamaguchi et al.
(Continued)

FOREIGN PATENT DOCUMENTS

EP 2127592 A1 12/2009
JP 2003-525074 A 8/2003
(Continued)

OTHER PUBLICATIONS

U.S. Appl. No. 18/378,395, filed Oct. 10, 2023.
(Continued)

*Primary Examiner* — Niketa Patel
*Assistant Examiner* — Sebastian X Lukjan
(74) *Attorney, Agent, or Firm* — Scully, Scott, Murphy & Presser, P.C.

(57) ABSTRACT

Provided is phototherapy progress measuring method for measuring a progress of a phototherapy of an affected portion by employing a fluorescent agent. The method includes: detecting a first fluorescence intensity, which is an intensity of fluorescence generated in the affected portion as a result of radiating therapeutic light beam onto the affected portion; and calculating, by employing the first fluorescence intensity and reference data, progress information representing the progress of the phototherapy of the affected portion. The reference data are determined on the basis of a fluorescence intensity associated with the fluorescent agent that is in the affected portion and that is not involved in the phototherapy.

18 Claims, 8 Drawing Sheets

(56) References Cited

U.S. PATENT DOCUMENTS

| | | | | |
|---|---|---|---|---|
| 2016/0016001 | A1* | 1/2016 | Loupis | H05B 45/20 604/20 |
| 2020/0214579 | A1 | 7/2020 | Phillips et al. | |
| 2021/0378494 | A1* | 12/2021 | Ishikawa | A61N 5/062 |

FOREIGN PATENT DOCUMENTS

| | | | |
|---|---|---|---|
| JP | 2006-167046 | A | 6/2006 |
| JP | 2008-148951 | A | 7/2008 |
| JP | 2008-539943 | A | 11/2008 |
| JP | 2011-104199 | A | 6/2011 |
| JP | 2011-212423 | A | 10/2011 |
| WO | 1999/006113 | A1 | 2/1999 |
| WO | 2001/005316 | A1 | 1/2001 |
| WO | 2006/121408 | A1 | 11/2006 |
| WO | 2008102803 | A1 | 8/2008 |
| WO | 2012/076631 | A1 | 6/2012 |
| WO | 2020/205623 | A1 | 10/2020 |
| WO | 2022/230173 | A1 | 11/2022 |

OTHER PUBLICATIONS

Yi Hong Ong, et al.,"Blood Flow Measurements Enable Optimization of Light Delivery for Personalized Photodynamic Therapy", Cancers (Basel), 12(6):1584(2020), https://doi.org/10.3390/cancers12061584.

Mayank Kumar, et al., "PulseCam: a camera-based, motion-robust and highly sensitive blood perfusion imaging modality", Scientific Reports, 10, 4825(2020), https://www.nature.com/articles/s41598-020-61576-0.

US Office Action dated Sep. 18, 2025 received in U.S. Appl. No. 18/378,395.

Japanese Office Action dated Jul. 1, 2025 received in 2023-517001.

International Search Report dated Jun. 1, 2021 received in PCT/JP2021/017201.

International Search Report dated Jun. 22, 2021 received in PCT/JP2021/017216.

H. Kobayashi, et al.,"Super enhanced permeability and retention (SUPR) effects in tumors following near infrared photoimmunotherapy", HHS Public Access, Nanoscale. Author manuscript; available in PMC Jan. 7, 2017., Retrieved from the Internet, URL:https://www.ncbi.nlm.nih.gov/pmc/articles/PMC4824660/pdf/nihms729385.pdf.

* cited by examiner 100
8
IMAGE ACQUISITION PORTION
5
IMAGE PROCESSING PORTION
101
6
DISPLAY PORTION
LIGHT DETECTION PORTION
11
INTENSITY-DATA GENERATION PORTION
12
COMPUTATION PORTION
14
DETERMINATION PORTION
15
10
STORAGE PORTION
13
THERAPEUTIC-LIGHT ADJUSTMENT PORTION
16
ILLUMINATION LIGHT SOURCE
2
THERAPEUTIC LIGHT SOURCE
3
1
7
7c
7d
7b
7a
4
L1
Lf
L2
A

FIG. 6

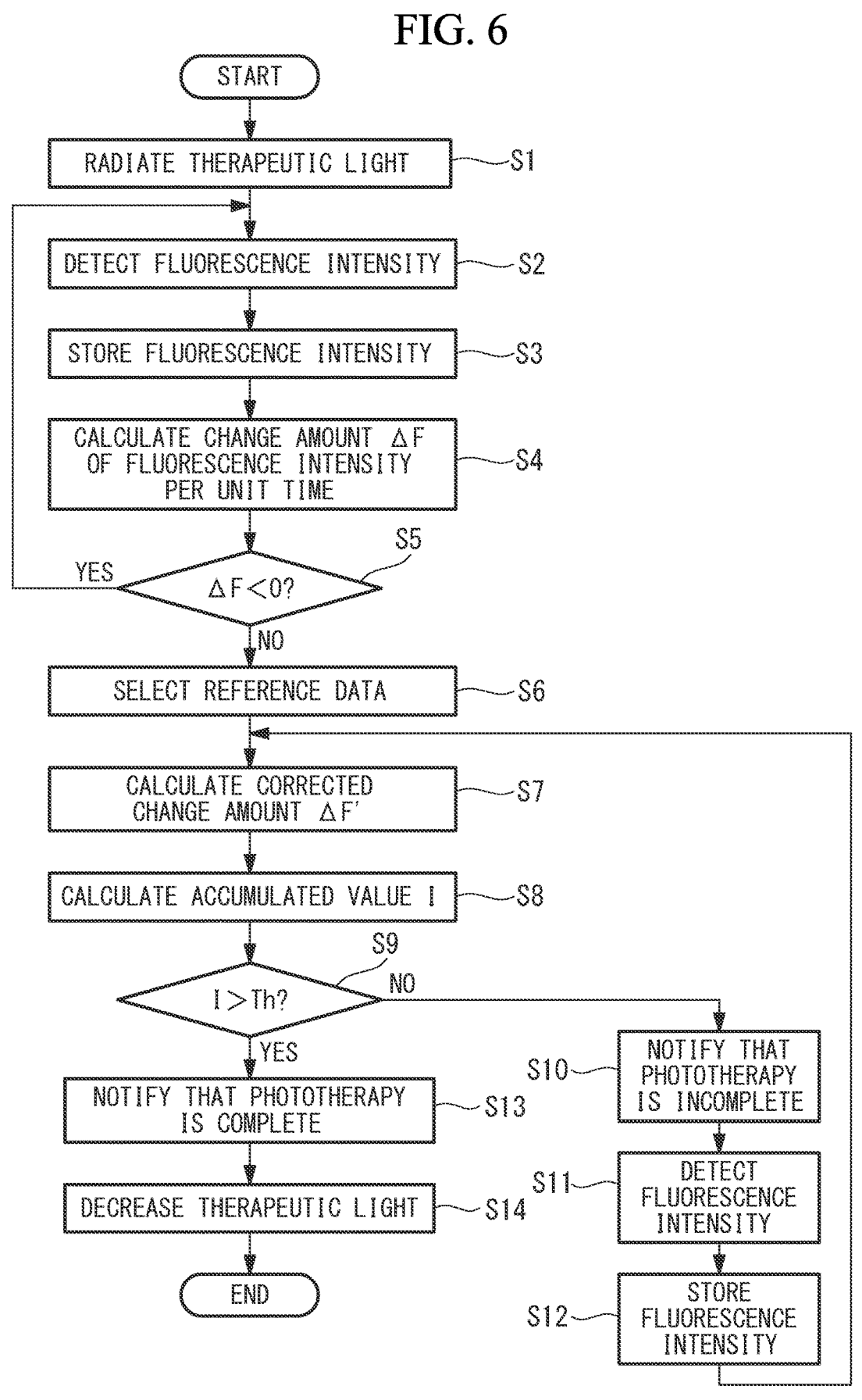

START
RADIATE THERAPEUTIC LIGHT S1
DETECT FLUORESCENCE INTENSITY S2
STORE FLUORESCENCE INTENSITY S3
CALCULATE CHANGE AMOUNT ΔF OF FLUORESCENCE INTENSITY PER UNIT TIME S4
ΔF<0? S5
YES
NO
SELECT REFERENCE DATA S6
CALCULATE CORRECTED CHANGE AMOUNT ΔF' S7
CALCULATE ACCUMULATED VALUE I S8
I>Th? S9
NO
NOTIFY THAT PHOTOTHERAPY IS INCOMPLETE S10
DETECT FLUORESCENCE INTENSITY S11
STORE FLUORESCENCE INTENSITY S12
YES
NOTIFY THAT PHOTOTHERAPY IS COMPLETE S13
DECREASE THERAPEUTIC LIGHT S14
END 200
8
IMAGE ACQUISITION PORTION
5
IMAGE PROCESSING PORTION
101
6
DISPLAY PORTION
LIGHT DETECTION PORTION
COMPUTATION PORTION
DETERMINATION PORTION
15
11
14
20
THERAPEUTIC-LIGHT ADJUSTMENT PORTION
16
1
7
ILLUMINATION LIGHT SOURCE
2
THERAPEUTIC LIGHT SOURCE
3
7c
7d
7b
7a
4
L1
Lf
L2, L3
A

PHOTOTHERAPY PROGRESS MEASURING METHOD, PROCESSOR, AND PHOTOTHERAPY SYSTEM

CROSS-REFERENCE TO RELATED APPLICATIONS

This is a continuation of International Application PCT/JP2021/017216 which is hereby incorporated by reference herein in its entirety.

TECHNICAL FIELD

The present invention relates to a phototherapy progress measuring method, a processor, and a phototherapy system.

BACKGROUND ART

In the related art, there is a known phototherapy in which an affected portion is treated by radiating therapeutic light beam onto the affected portion to excite a fluorescent agent in the affected portion (for example, see Patent Literature 1). The fluorescent agent is consumed with the progress of phototherapy and, in association with the consumption of the fluorescent agent, the intensity of fluorescence generated in the affected portion attenuates. In Patent Literature 1, the irradiation of the affected portion with the therapeutic light beam is ended when the fluorescence intensity becomes equal to or less than a prescribed threshold.

CITATION LIST

Patent Literature

{PTL 1} Japanese Unexamined Patent Application, Publication No. 2006-167046

SUMMARY OF INVENTION

An aspect of the present invention is a phototherapy progress measuring method for measuring a progress of a phototherapy of an affected portion by employing a fluorescent agent, the method including: detecting a first fluorescence intensity, which is an intensity of fluorescence generated in the affected portion as a result of radiating therapeutic light beam onto the affected portion; and calculating, by employing the first fluorescence intensity and reference data, progress information representing the progress of the phototherapy of the affected portion, wherein the reference data are determined on the basis of a fluorescence intensity associated with the fluorescent agent that is in the affected portion and that is not involved in the phototherapy.

Another aspect of the present invention is a processor that measures a progress of a phototherapy of an affected portion by employing a fluorescent agent, the processor including: a light detection portion that detects a first fluorescence intensity, which is an intensity of fluorescence generated in the affected portion as a result of radiating therapeutic light beam onto the affected portion; and a computation portion that calculates, by employing the first fluorescence intensity and reference data, progress information representing the progress of the phototherapy of the affected portion, wherein the reference data are determined on the basis of a fluorescence intensity associated with the fluorescent agent that is in the affected portion and that is not involved in the phototherapy.

Another aspect of the present invention is a phototherapy system that performs a phototherapy of an affected portion by means of a fluorescent agent by radiating therapeutic light beam onto the affected portion, the system including: a therapeutic light source that outputs the therapeutic light beam; a probe that radiates the therapeutic light beam onto the affected portion; and the above-described processor, wherein the processor outputs determination results.

BRIEF DESCRIPTION OF DRAWINGS

FIG. 6 is a flowchart showing the operations of the phototherapy progress measuring device and the phototherapy system in FIG. 1.

DESCRIPTION OF EMBODIMENTS

First Embodiment

A phototherapy progress measuring method, a phototherapy progress measuring device, and a phototherapy system according to a first embodiment of the present invention will be described with reference to the drawings.

Figure 1:
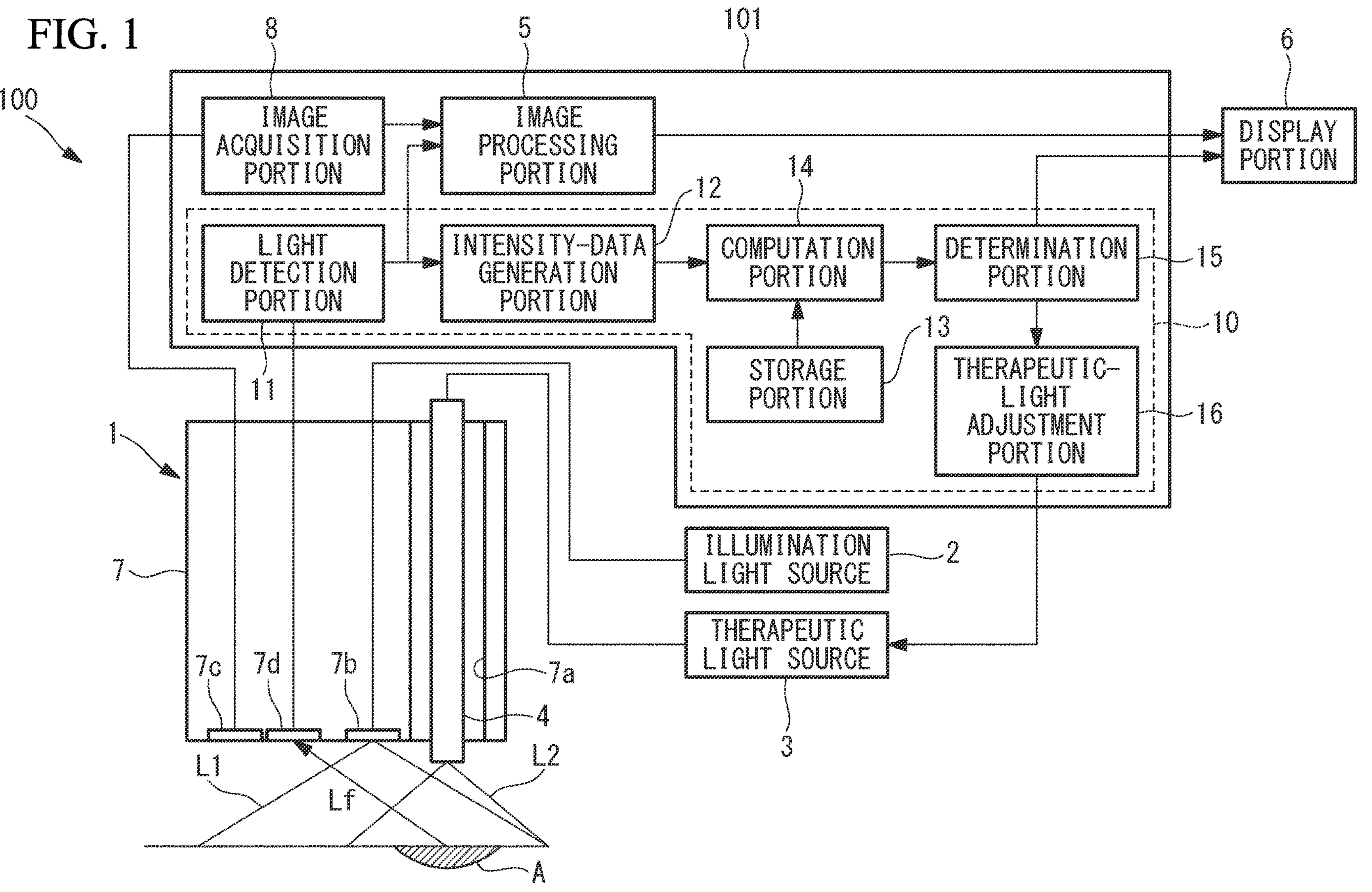
FIG. 1 is an overall configuration diagram of a phototherapy progress measuring device and a phototherapy system according to a first embodiment.

As shown in FIG. 1, a phototherapy system 100 according to this embodiment is an endoscope system in which phototherapy of an affected portion A is performed by means of a photoresponsive fluorescent agent while observing the affected portion A with an endoscope 1. The affected portion A is, for example, cancer of the upper gastrointestinal tract, such as the esophagus. The fluorescent agent is a fluorescent molecule that has the property of accumulating in the affected portion A and exhibits a therapeutic effect by being activated as a result of being excited by excitation light. The fluorescent agent is, for example, a panitumumab-IR700 complex or a hematoporphyrin derivative.

The phototherapy system 100 includes: the endoscope 1 for observing the affected portion A in a body; an illumination light source 2 that generates an illumination light beam L1 for illuminating the affected portion A; a therapeutic light source 3 that generates a therapeutic light beam L2 for treating the affected portion A; a probe (therapeutic-light irradiation portion) 4 that is inserted into the body via the endoscope 1 and that radiates the therapeutic light beam L2 onto the affected portion A; an image processing portion 5 that processes an endoscope image; and a display portion (notification portion) 6 that displays the endoscope image. A basal end of the endoscope 1 is connected to an endoscope processor 101.

The endoscope 1 has a flexible or rigid elongated scope 7 and an image acquisition portion 8. The scope 7 is provided with a treatment-tool channel 7*a* that passes through the scope 7 in a longitudinal direction thereof. In addition, a distal-end surface of the scope 7 is provided with an illumination window 7*b* and a light reception window 7*c*. The endoscope 1 emits the illumination light beam L1 supplied thereto from the illumination light source 2 toward the affected portion A from the illumination window 7*b*. In addition, the endoscope 1 receives the illumination light beam L1 reflected at the affected portion A in the light reception window 7*c* and acquires an endoscope image of the affected portion A by means of the image acquisition portion 8 having an imaging element.

The illumination light source 2 outputs the white illumination light beam L1.

The therapeutic light source 3 outputs the therapeutic light beam L2, which is excitation light having an excitation wavelength for the fluorescent agent.

The probe 4 is an elongated optical fiber probe having an optical fiber that guides the therapeutic light beam L2 and is inserted into the treatment-tool channel 7*a*. A basal end of the probe 4 is connected to the therapeutic light source 3 and the therapeutic light beam L2 is radiated onto the affected portion A from a distal end of the probe 4.

The image processing portion 5 receives the endoscope image from the image acquisition portion 8 and outputs the endoscope image to the display portion 6 after applying processing to the endoscope image, as needed.

The display portion 6 is an arbitrary display device such as a liquid crystal display.

Figure 2:
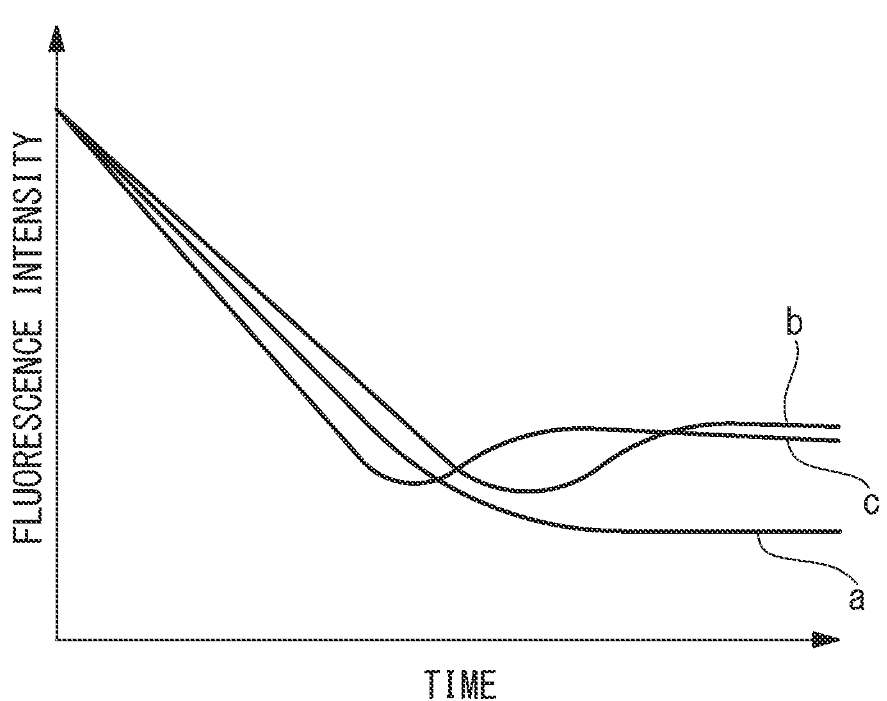
FIG. 2 is a diagram showing an example of the temporal change of the fluorescence intensity in an affected portion during phototherapy.

FIG. 2 relates to experimental results of phototherapy employing a Panitumumab-IR700 complex, which is a complex formed of a molecular target antibody and a fluorescent substance. The fluorescent agent in the affected portion A is consumed during the progress of the phototherapy, and, in association with the consumption of the fluorescent agent, a fluorescence intensity F attenuates. Therefore, a doctor can recognize the progress of phototherapy on the basis of the attenuation of the fluorescence intensity F. However, the fluorescence intensity F does not necessarily monotonically attenuate, as in a curve a, and there are cases in which the fluorescence intensity F increases in the final stage of phototherapy, as in curves b and c. In addition, the attenuation rate of the fluorescence intensity F also differs depending on the conditions, etc. Therefore, it is difficult to determine whether the necessary quantity of the fluorescent agent administered in the affected portion A has been consumed, in other words, whether the phototherapy has been completed, only on the basis of the fluorescence intensity F.

Figure 3:
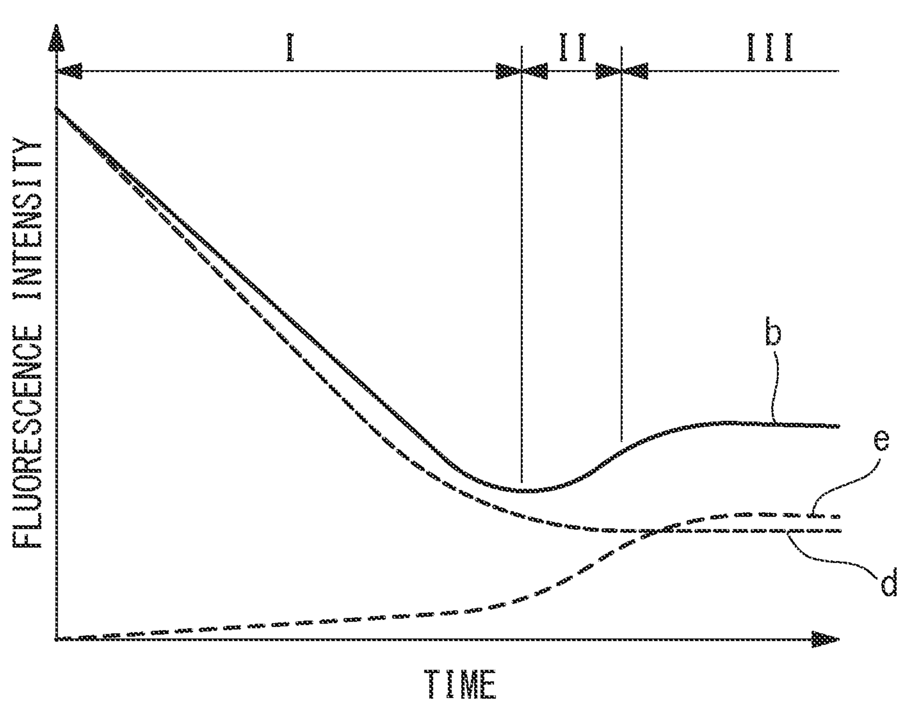
FIG. 3 is a diagram for explaining the fluorescence intensity in the affected portion.

One of the reasons why the fluorescence intensity F does not monotonically attenuate is assumed to be re-accumulation of the fluorescent agent during phototherapy. In other words, after a sufficient quantity of the fluorescent agent is administered to a patient by means of an intravenous injection, some of the fluorescent agent re-circulates together with blood without being taken up by the affected portion A and re-accumulates in the affected portion A in the final stage of phototherapy, and thus, the fluorescence intensity F increases. As shown in FIG. 3, the fluorescence intensity F (see the curve b) is the sum of the intensity (see curve d) of fluorescence generated by the fluorescent agent that has accumulated in advance in the affected portion A before starting the phototherapy and the intensity (see curve e) of fluorescence generated by the fluorescent agent that re-accumulates in the affected portion A after phototherapy has started.

In the period I, the fluorescence generated by the fluorescent agent that has accumulated in advance in the affected portion A before the phototherapy is dominant, and a high therapeutic effect is achieved. In the period II, the fluorescence generated by the fluorescent agent that has accumulated in advance and the fluorescence generated by the fluorescent agent that has re-accumulated are mixed, and only a slight therapeutic effect is achieved. In the period III, the fluorescence generated by the re-accumulated fluorescent agent is dominant, and almost no phototherapeutic effect due to the fluorescent agent accumulated in advance in the affected portion A is achieved.

The phototherapy system 100 includes a phototherapy progress measuring device 10 that measures the progress of the phototherapy of the affected portion A in order to assist the doctor to determine whether to end the phototherapy of the affected portion A. As shown in FIG. 1, the phototherapy progress measuring device 10 includes: a light detection portion 11 that detects a fluorescence intensity (first fluorescence intensity) F; an intensity-data generation portion 12 that stores the detected the fluorescence intensity F in a time sequence; a storage portion 13 that stores a plurality of preset data that are prepared in advance; a computation portion 14 that calculates progress information that represents the progress of the phototherapy of the affected portion A; a determination portion 15 that determines whether the phototherapy of the affected portion A has been completed on the basis of the progress information; and a therapeutic-light adjustment portion 16 that adjusts the intensity of the therapeutic light beam L2.

The phototherapy progress measuring device 10 has at least one processor, such as a central processing unit, and a storage device, such as a RAM (random access memory) or a ROM (read-only memory). Processing by the intensity-data generation portion 12, the computation portion 14, the determination portion 15, and the therapeutic-light adjustment portion 16, described later, is realized as a result of the processor executing the processing in accordance with programs stored in the storage device. The storage portion 13 consists of a storage device.

A distal-end surface of the scope 7 is provided with a barrier filter 7*d* that selectively transmits fluorescence Lf and blocks light in a wavelength range differing from that of the selectively transmitted fluorescence Lf. The light detection portion 11 detects the intensity F of the fluorescence Lf transmitted through the barrier filter 7*d* and transmits the fluorescence intensity F to the intensity-data generation portion 12. For example, the light detection portion 11 has an imaging element provided in the endoscope processor 101 or in the scope 7 and acquires fluorescence images containing information about the fluorescence intensity F. The fluorescence images may be transmitted to the display portion 6 via the image processing portion 5 and displayed on the display portion 6. The light detection portion 11 may have an arbitrary type of photodetector other than the imaging element.

The intensity-data generation portion 12 generates intensity data by storing the fluorescence intensity F in a time sequence. For example, the intensity-data generation portion 12 stores the average luminance value of the fluorescence images as an intensity value. The intensity data are data that represent a temporal change of the fluorescence intensity F, as in the curves a, b, and c shown in FIGS. 2 and 3.

Figure 4:
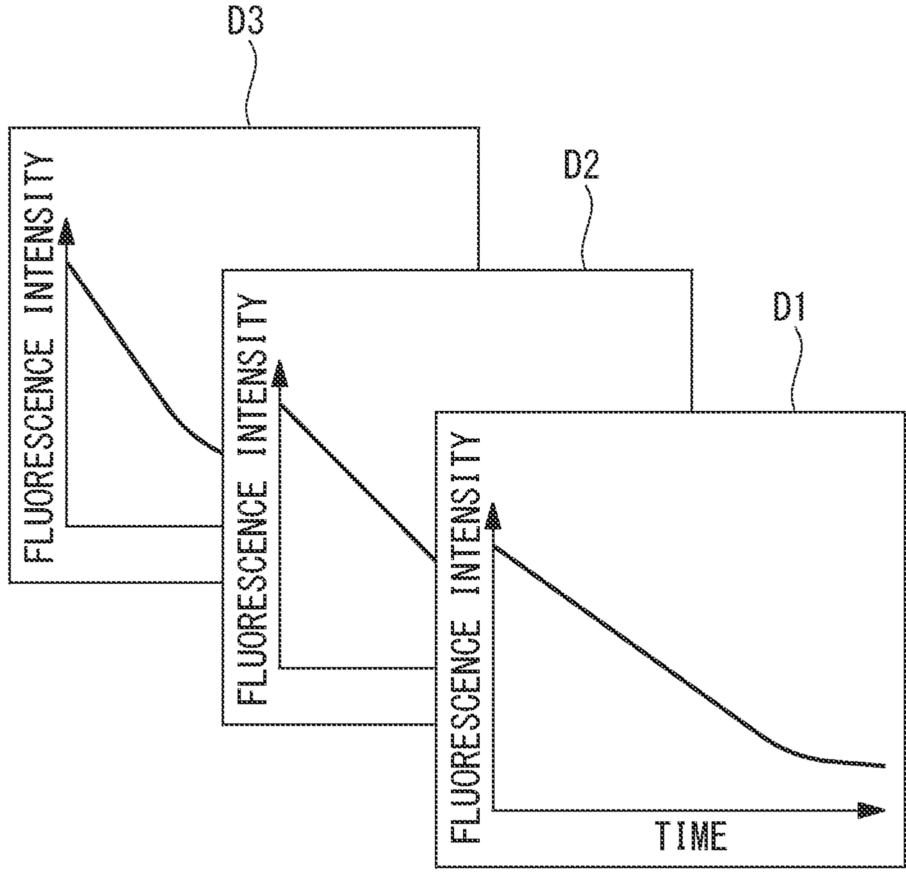
FIG. 4 is a diagram showing a plurality of preset data stored in a storage portion.

As shown in FIG. 4, a plurality of preset data D1, D2, D3 . . . stored in advance in the storage portion 13 are data representing the temporal change of the fluorescence intensity of the fluorescent agent due to the irradiation of the therapeutic light beam L2, excluding the fluorescence intensity of the re-accumulating fluorescent agent.

For example, the preset data D1, D2, D3 . . . are acquired by detecting and storing, in a time sequence manner, the fluorescence intensity by radiating the therapeutic light beam L2 onto the fluorescent agent in a test tube and stored in the storage portion 13 by an operator before a phototherapy is performed. The manner in which the fluorescence intensity attenuates in the affected portion A changes in accordance with various parameters such as the measurement distance, the fluorescent agent concentration, and the irradiation intensity of the therapeutic light beam L2. Therefore, the storage portion 13 stores the plurality of preset data D1, D2, D3 . . . that are acquired by using different parameters.

The computation portion 14 determines, in real time, whether the fluorescence intensity F is attenuating and starts to calculate the progress information by employing the intensity data and the preset data when the fluorescence intensity F stops attenuating for the first time.

Specifically, the computation portion 14 calculates, each time the fluorescence intensity F is detected by the light detection portion 11, a change amount ΔF of the fluorescence intensity F per unit time at that point in time. For example, in the case in which a fluorescence intensity $F(t_i)$ is detected at a time $t_i$ (i=1, 2, 3 . . . ), a change amount $\Delta F(t_i)$ at the time ti is calculated from the following formula by employing the fluorescence intensity $F(t_i)$ and a fluorescence intensity $F(t_{i-1})$ detected at an immediately preceding time $t_{i-1}$.

$$\Delta F(t_i)=(F(t_i)-F(t_{i-1}))/(t_i-t_{i-1})$$

In the case in which the change amount ΔF is negative, in other words, in the case in which the fluorescence intensity F is attenuating, the computation portion 14 does not calculate the progress information. In the case in which the change amount ΔF is not negative, in other words, in the case in which the change amount ΔF is zero or positive and the fluorescence intensity F is constant or increasing, the computation portion 14 executes processing, described later, for calculating the progress information.

Figure 5:
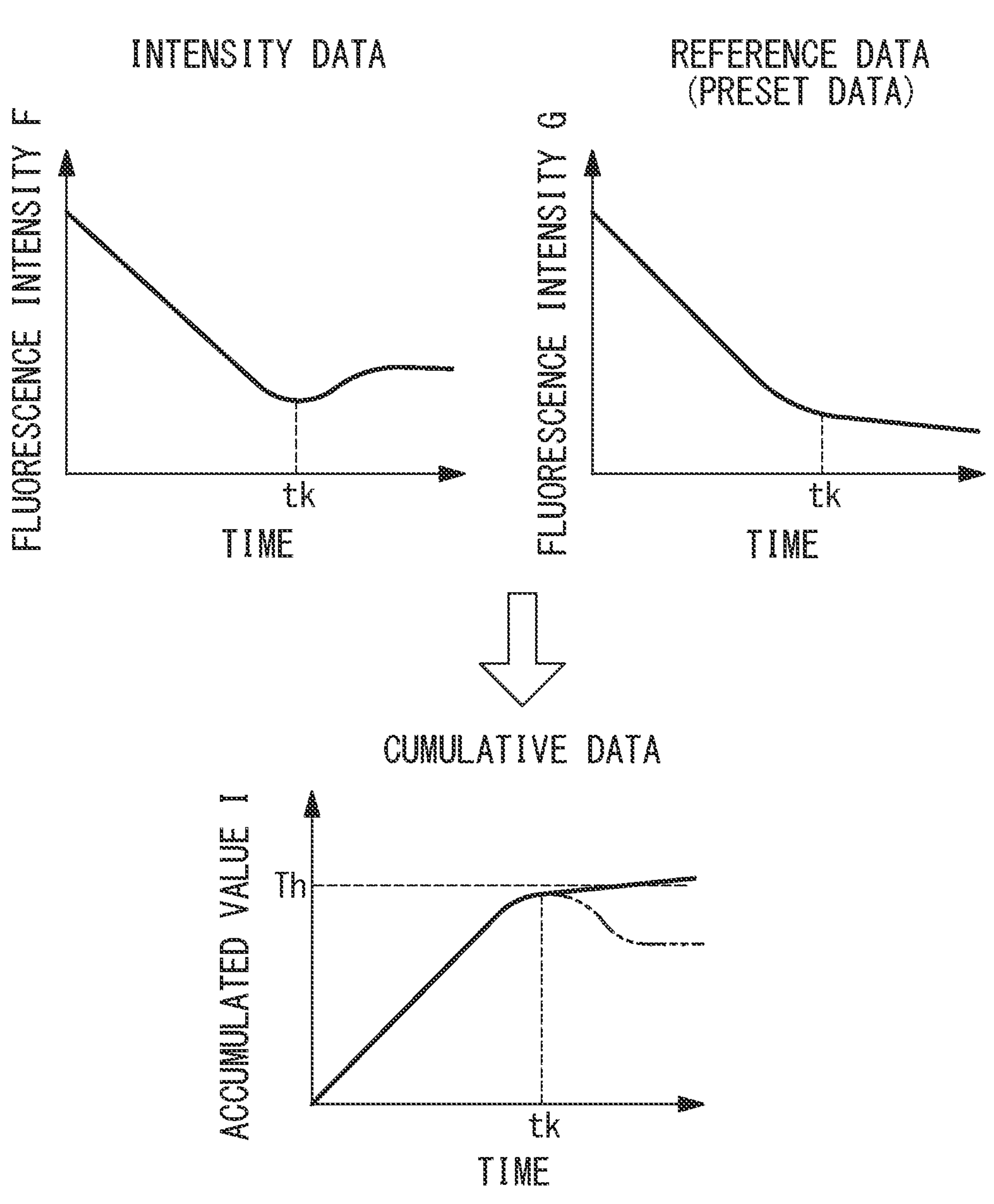
FIG. 5 is a diagram for explaining an accumulated-value calculation method employing the preset data.

FIG. 5 describes a calculation method for the progress information employing the intensity data and the preset data.

The progress information is an accumulated value I obtained by accumulating the change amount of the fluorescence intensity F per unit time from the start of treatment to the current point in time. FIG. 5 shows cumulative data representing the temporal change of the accumulated value I. The accumulated value I represents the amount of the fluorescent agent consumed in the affected portion A due to the irradiation of the affected portion A with the therapeutic light beam L2, in other words, the progress of the phototherapy of the affected portion A.

As shown in FIG. 5, the computation portion 14 selects, from among the plurality of preset data, one preset data that is most similar to the intensity data so as to serve as reference data. Specifically, the computation portion 14 compares a curve of the temporal change of the fluorescence intensity F in the intensity data with a curve of temporal change of fluorescence intensity G in the plurality of preset data, and selects preset data in which the curve thereof has a shape that is most similar to the curve of the intensity data.

Next, the computation portion 14 calculates a corrected change amount ΔF' after it is determined for the first time that the change amount ΔF is not negative by employing the reference data and calculates the accumulated value I by employing the corrected change amount ΔF' and the change amount ΔF before it is determined for the first time that the change amount ΔF is not negative. In FIG. 5, a time $t_k$ is a time at which it is determined for the first time that the change amount ΔF is not negative.

The corrected change amount ΔF' corresponds to a change amount ΔF corrected so as to remove the change amount of the fluorescence intensity per unit time of the fluorescent agent that re-accumulates in the affected portion A and is a net change amount of the fluorescence intensity of the fluorescent agent that has accumulated in advance in the affected portion A expected in the case in which there is no re-accumulation of the fluorescent agent in the affected portion A. In the case in which the accumulated value I is calculated by employing only the change amount ΔF, the accumulated value I is influenced by the fluorescence intensity of the re-accumulating fluorescent agent as indicated by the chain line in the cumulative data in FIG. 5 and, for example, stops monotonically increasing. In contrast, as a result of employing the corrected change amount ΔF' instead of the change amount ΔF after it is determined for the first time that the change amount ΔF is not negative, it is possible to calculate the accumulated value I in which the influence of the fluorescence intensity of the re-accumulating fluorescent agent is removed, as indicated by the solid line in the cumulative data in FIG. 5.

Specifically, the computation portion 14 calculates, as a correction factor, an attenuation rate α of the fluorescence intensity G per unit time at a time corresponding to the current point in time. An attenuation rate $\alpha(t_i)$ at a time $t_i$ is calculated from the following formula by employing fluorescence intensities $G(t_i)$ and $G(t_{i-1})$ at times $t_i$ and $t_{i-1}$.

$$\alpha(t_i)=1-G(t_i)/G(t_{i-1})$$

Next, the computation portion 14 calculates a corrected change amount $\Delta F'(t_i)$ at the current point in time $t_i$ by multiplying the fluorescence intensity $F(t_{i-1})$ detected immediately before the fluorescence intensity $F(t_i)$ by the attenuation rate $\alpha(t_i)$. Next, the computation portion 14 calculates an accumulated value $I(t_i)$ by adding the corrected change amount $\Delta F'(t_i)$ to an accumulated value $I(t_{i-1})$ at a time $t_{i-1}$. The computation portion 14 calculates the attenuation rate α, the corrected change amount ΔF', and the accumulated value I each time the fluorescence intensity F is detected.

The determination portion 15 compares the accumulated value I with a prescribed threshold Th. In the case in which the accumulated value I is equal to or less than the threshold Th, the determination portion 15 outputs a determination result indicating that the accumulated value I has become equal to or less than the prescribed threshold. In the case in which the accumulated value I is greater than the threshold Th, the determination portion 15 outputs a determination result indicating that the accumulated value I has exceeded the prescribed threshold. The determination results of the determination portion 15 are transmitted to the therapeutic-light adjustment portion 16 and notified to the doctor by being displayed on the display portion 6.

The therapeutic-light adjustment portion 16 adjusts the intensity of the therapeutic light beam L2 radiated onto the affected portion A on the basis of the determination results of the determination portion 15. Specifically, in the case in which it is determined that the accumulated value I is equal to or less than the prescribed threshold, the therapeutic-light adjustment portion 16 maintains the intensity of the therapeutic light beam L2 radiated onto the affected portion A by maintaining the output of the therapeutic light beam L2 from the therapeutic light source 3. On the other hand, in the case in which it is determined that the accumulated value I has exceeded the prescribed threshold, the therapeutic-light adjustment portion 16 decreases the intensity of the therapeutic light beam L2 radiated onto the affected portion A by decreasing or stopping the output of the therapeutic light beam L2 from the therapeutic light source 3 by controlling the therapeutic light source 3.

Next, the operations of the phototherapy system 100 and the phototherapy progress measuring device 10 will be described with reference to FIG. 6.

In order to perform phototherapy of an affected portion A by using the phototherapy system 100, first, the fluorescent agent is administered to the affected portion A by applying, for example, an intravenous injection to a patient. After performing the intravenous injection, it takes time for the fluorescent agent to accumulate in the affected portion A. After a prescribed amount of time (for example, 24 hours) has passed from the intravenous injection, a doctor turns on the illumination light source 2, inserts the endoscope 1 into the body of the patient while observing an endoscope image displayed on the display portion 6, and disposes the distal end of the endoscope 1 in the vicinity of the affected portion A. Next, the doctor inserts the probe 4 into the body via the treatment-tool channel 7*a* of the endoscope 1 to dispose the distal end of the probe 4 in the vicinity of the affected portion A and turns on the therapeutic light source 3. Accordingly, the irradiation of the affected portion A with the therapeutic light beam L2 from the distal end of the probe 4 is started, and the phototherapy of the affected portion A is started (step S1).

During the phototherapy, the doctor checks the progress of the phototherapy on the basis of the attenuation of the fluorescence intensity F of the affected portion A in the endoscope image displayed on the display portion 6. However, because the fluorescence intensity F is influenced by the fluorescent agent that re-accumulates in the affected portion A during the phototherapy, the fluorescence intensity F does not necessarily accurately represent the progress of the phototherapy. Therefore, it is difficult to determine whether the phototherapy has been completed only on the basis of the fluorescence intensity F.

With this embodiment, a phototherapy progress measuring method is executed by the phototherapy progress measuring device 10 during the phototherapy.

The phototherapy progress measuring method includes: steps S2 and S11 for detecting the intensity F of the fluorescence Lf generated in the affected portion A due to the irradiation with the therapeutic light beam L2; steps S3 and S12 for storing the fluorescence intensity F and generating the intensity data representing the temporal changes in the fluorescence intensity F; steps S4 and S5 for determining the change amount ΔF of the fluorescence intensity F; steps S6 to S8 for calculating the progress information representing the progress of the phototherapy; and a step S9 for determining whether the phototherapy of the affected portion A has been completed on the basis of the progress information.

After starting the phototherapy, the light detection portion 11 detects the fluorescence intensity F (step S2) and the intensity-data generation portion 12 stores the fluorescence intensity F in a time sequence and generates the intensity data (step S3). Next, the computation portion 14 calculates the change amount ΔF of the fluorescence intensity F per unit time (step S4) and it is determined whether the change amount ΔF is negative, in other words, whether the fluorescence intensity F is monotonically attenuating (step S5). In the case in which the change amount ΔF is negative ("YES" in step S5), steps S2 to S4 are repeated.

In the case in which the change amount ΔF is not negative ("NO" in step S5), the computation portion 14 calculates the progress information of the affected portion A by employing the intensity data and the reference data (steps S6 to S8). Specifically, from among the plurality of preset data, preset data that are most similar to the intensity data are selected as the reference data (step S6). Next, the computation portion 14 calculates the corrected change amount ΔF' of the fluorescence intensity F by employing the reference data, and calculates the accumulated value I, which is the progress information, by employing the change amount ΔF calculated in step S4 and the corrected change amount ΔF'.

Next, the determination portion 15 compares the accumulated value I with the prescribed threshold Th (step S9). In the case in which it is determined that the accumulated value I is equal to or less than the threshold Th ("NO" in step S9), and, as a result of the information indicating that the phototherapy is incomplete being displayed on the display portion 6, the doctor is notified that the phototherapy is incomplete (step S10). Subsequently, the detection of the fluorescence intensity F, the intensity data generation, and the progress information calculation in steps S11, S12, S7, and S8 are repeated until it is determined that the accumulated value I is equal to or less than the threshold Th.

In the case in which it is determined that the accumulated value I is greater than the threshold Th ("YES" in step S9), as a result of the information indicating that the phototherapy has been completed being displayed on the display portion 6, the doctor is notified that the phototherapy has been completed (step S13). In addition, the therapeutic-light adjustment portion 16 decreases the intensity of the therapeutic light beam L2 radiated onto the affected portion A (step S14).

The doctor determines whether to end the phototherapy on the basis of the determination results displayed on the display portion 6. Specifically, in the case in which the determination result indicating that the accumulated value I is equal to or less than the prescribed threshold Th is output, the doctor continues to radiate the therapeutic light beam L2 onto the affected portion A. On the other hand, in the case in which the determination result indicating that the accumulated value I has exceeded the prescribed threshold Th is output, the doctor ends the irradiation of the affected portion A with the therapeutic light beam L2 by turning off the therapeutic light source 3 and ends the phototherapy of the affected portion A.

As has been described above, it is difficult for the doctor to determine whether phototherapy has been completed only on the basis of the fluorescence intensity F of the affected portion A during the phototherapy. With this embodiment, the storage portion 13 stores the plurality of preset data D1, D2, D3 . . . that are prepared in advance. The preset data D1, D2 . . . are data of the fluorescence intensity of the fluorescent agent that monotonically decreases due to the irradiation with the therapeutic light beam L2, excluding the fluorescence intensity of the re-accumulating fluorescent agent. In other words, the preset data D1, D2, D3 . . . are models of typical temporal changes of the fluorescence intensity F of the affected portion A due to the irradiation with the therapeutic light beam L2 in the case in which the re-accumulation of the fluorescent agent in the affected portion A does not occur during the phototherapy.

By employing any one of such preset data D1, D2, D3 . . . , the corrected change amount ΔF' in which the change amount of the fluorescence intensity of the re-accumulating fluorescent agent per unit time is removed is calculated. Thus, it is possible to calculate, as the progress information, the accumulated value I, which represents the accurate amounts of the fluorescent agent consumed due to the phototherapy, by employing the corrected change amount ΔF', and it is possible to measure the accurate progress of the phototherapy. In addition, it is possible to accurately determine whether the phototherapy has been completed on the basis of the progress information.

In addition, the fluorescence intensity F is a parameter that is directly related to the consumed amount of the fluorescent agent in the affected portion A, and it is possible to calculate, in real time, the progress information from the fluorescence intensity F. Accordingly, it is possible to measure, in real time, the accurate progress of the phototherapy and to determine, in real time, whether the phototherapy has been completed.

In the case in which the progress of the phototherapy is indirectly measured by employing information other than the fluorescence intensity, it is difficult to measure, in real time, the progress of the phototherapy.

In this embodiment, the corrected change amount ΔF' is calculated by multiplying the fluorescence intensity F by the attenuation rate α calculated from the reference data; however, the calculation method for the corrected change amount ΔF' is not limited thereto, and an arbitrary calculation method can be employed so long as it is possible to calculate the net change amount ΔF' that is due to the fluorescent agent that has accumulated in advance in the affected portion and in which the change amount due to the re-accumulating fluorescent agent is removed.

In one modification, after it is determined for the first time that the fluorescence intensity F does not attenuate, a change amount $\Delta G(t_i)$ of the fluorescence intensity $G(t_i)$ per unit time, which is the reference data, may be employed as the corrected change amount $\Delta F'(t_i)$.

In another modification, after it is determined for the first time that the fluorescence intensity F does not attenuate, the fluorescence intensity $G(t_i)$, which is the reference data, may be employed as the fluorescence intensity $F(t_i)$, which is the intensity data. In other words, the fluorescence intensity F, which is the intensity data, after it is determined for the first time that the fluorescence intensity F does not attenuate, is replaced with the fluorescence intensity G, which is the reference data, and the change amount ΔG of the fluorescence intensity G per unit time is calculated as the corrected change amount ΔF'.

With these modifications, because the corrected change amount ΔF' is predicted only from the reference data, it is not necessary to detect and store the fluorescence intensity F after it is determined for the first time that the fluorescence intensity F does not attenuate. Therefore, it is possible to simplify the processing required to calculate the progress information.

Second Embodiment

Next, a phototherapy progress measuring method, a phototherapy progress measuring device, and a phototherapy system according to a second embodiment of the present invention will be described with reference to the drawings.

A phototherapy system 200 according to this embodiment differs from the phototherapy system 100 according to the first embodiment in that a phototherapy progress measuring device 20 acquires, as reference data, data of a second fluorescence intensity, which is the fluorescence intensity of the re-accumulated fluorescent agent, and calculates the progress information by employing the data of the second fluorescence intensity. In this embodiment, features differing from the first embodiment will be described, and configurations that are the same as those of the first embodiment will be given the same reference signs and descriptions thereof will be omitted.

Figure 7:
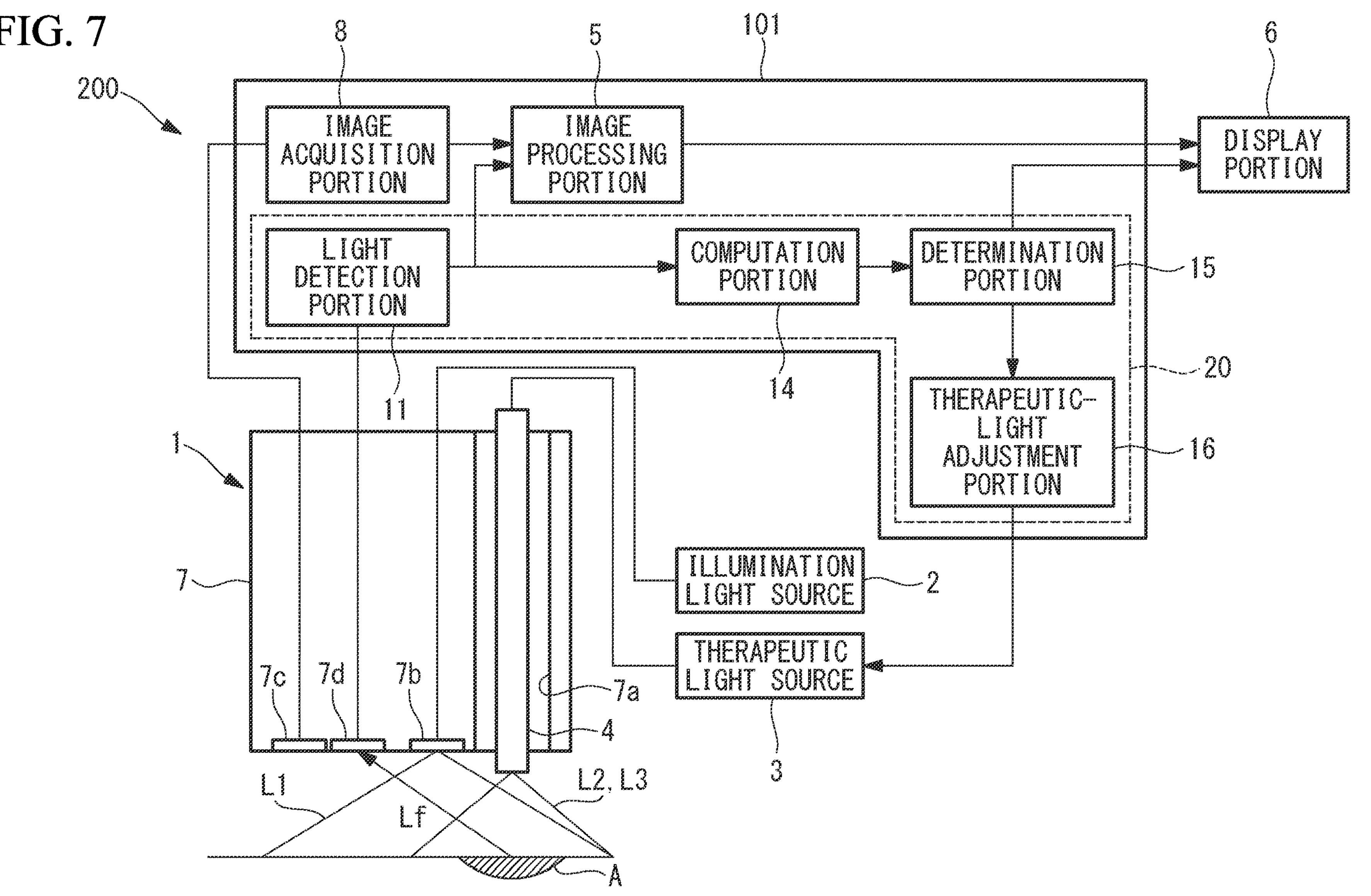
FIG. 7 is an overall configuration diagram of a phototherapy progress measuring device and a phototherapy system according to a second embodiment.

As shown in FIG. 7, the phototherapy system 200 includes: the endoscope 1; the illumination light source 2; the therapeutic light source 3; the probe 4; the image processing portion 5; the display portion 6; and the phototherapy progress measuring device 20.

The phototherapy progress measuring device 20 incudes: the light detection portion 11; the computation portion 14; the determination portion 15; and the therapeutic-light adjustment portion 16.

In this embodiment, the therapeutic-light adjustment portion 16 switches the output of the therapeutic light source 3 between a high-output first output and a low-output second output to switch the light radiated onto the affected portion A between the therapeutic light beam L2 and measurement light beam L3. The therapeutic light beam L2 is light having a first intensity required for the phototherapy. Although the fluorescent agent emits fluorescence in the form of excitation light having an arbitrary light intensity, the fluorescent agent exhibits the phototherapeutic effect only at a sufficiently high light intensity. The fluorescent agent exhibiting the phototherapeutic effect has properties of not emitting fluorescence due to a loss of the molecular structure of the fluorescent molecule. The measurement light beam L3 has a second intensity that is lower than the first intensity and is weak light that does not cause the fluorescent agent to exhibit the phototherapeutic effect. In other words, the measurement light beam L3 is the therapeutic light beam L2 that has been attenuated. For example, the first intensity is about 100 mW and the second intensity is several nanowatts. The measurement light beam L3 acts on both the unconsumed fluorescent agent that has accumulated in advance in the affected portion and the fluorescent agent that has re-accumulated in the affected portion A and that is not bound to the affected portion A, and generates the fluorescence Lf in the form of the sum of fluorescence from the fluorescent agent in these two states.

The light detection portion 11 detects the first fluorescence intensity F1 and the second fluorescence intensity F2 in an alternating manner and outputs the fluorescence intensities F1 and F2 to the computation portion 14. The first fluorescence intensity F1 is the intensity of the fluorescence Lf generated in the affected portion A due to the irradiation with the therapeutic light beam L2 and is the intensity of the fluorescence Lf generated by the fluorescent agent that has accumulated in advance in the affected portion A and the re-accumulated fluorescent agent therein. The second fluorescence intensity F2 is the intensity of the fluorescence Lf generated in the affected portion A due to the irradiation with the measurement light beam L3 and is the intensity of the fluorescence generated by the fluorescent agent that has re-accumulated in the affected portion A. In order for the computation portion 14 to distinguish the first fluorescence intensity F1 and the second fluorescence intensity F2, the first fluorescence intensity F1 and the second fluorescence intensity F2 are associated with the therapeutic light beam L2 and the measurement light beam L3, respectively.

The computation portion 14 calculates, each time the light detection portion 11 detects the first fluorescence intensity F1, the change amount ΔF1 of the first fluorescence intensity F1 per unit time at that point in time, and calculates, each time the light detection portion 11 detects the second fluorescence intensity F2, the change amount ΔF2 of the second fluorescence intensity F2 per unit time at that point in time. The change amounts ΔF1 and ΔF2 are calculated by using the same method as for the change amount ΔF in the first embodiment. Next, the computation portion 14 calculates, as the progress information, a degree of agreement between the change amount ΔF1 and the change amount ΔF2. For example, the degree of agreement is expressed by employing the difference or the ratio between the change amounts ΔF1 and ΔF2, and the degree of agreement increases as the difference between the change amounts ΔF1 and ΔF2 approaches zero.

Figure 8:
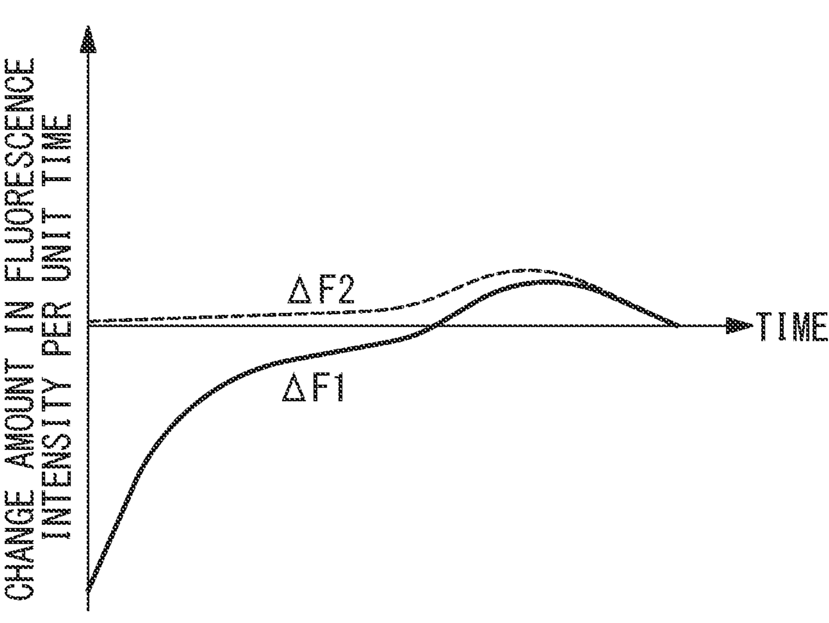
FIG. 8 is a diagram showing an example of the temporal change of a first fluorescence intensity per unit time and an example of a temporal change of a second fluorescence intensity per unit time.

As shown in FIG. 8, when the phototherapy of the affected portion A has been completed, because the change in the fluorescence intensity F2 of the re-accumulated fluorescent agent is dominant over the change in the fluorescence intensity F1 of the affected portion A, the change amount ΔF1 is equal to or substantially equal to the change amount ΔF2. Therefore, with the phototherapy of the affected portion A approaching to completion, the degree of agreement increases.

The change amount ΔF1 and the change amount ΔF2 are quantities based on the light beams L2 and L3 having different intensities. Therefore, the change amounts ΔF1 and ΔF2 may be standardized so that the change amounts ΔF1 and ΔF2 take values for the case in which the light beams L2 and L3 having the same intensity are irradiated, and the degree of agreement may be calculated by employing the standardized change amounts ΔF1 and ΔF2.

The determination portion 15 compares the degree of agreement with a prescribed threshold Th. In the case in which the degree of agreement is equal to or less than the threshold Th, the determination portion 15 outputs a determination result indicating that the degree of agreement is equal to or less than the prescribed threshold Th. In the case in which the degree of agreement is greater than the threshold Th, the determination portion 15 outputs a determination result indicating that the degree of agreement has exceeded the prescribed threshold Th.

Next, the operations of the phototherapy system 200 and the phototherapy progress measuring device 20 will be described with reference to FIG. 9.

Figure 9:
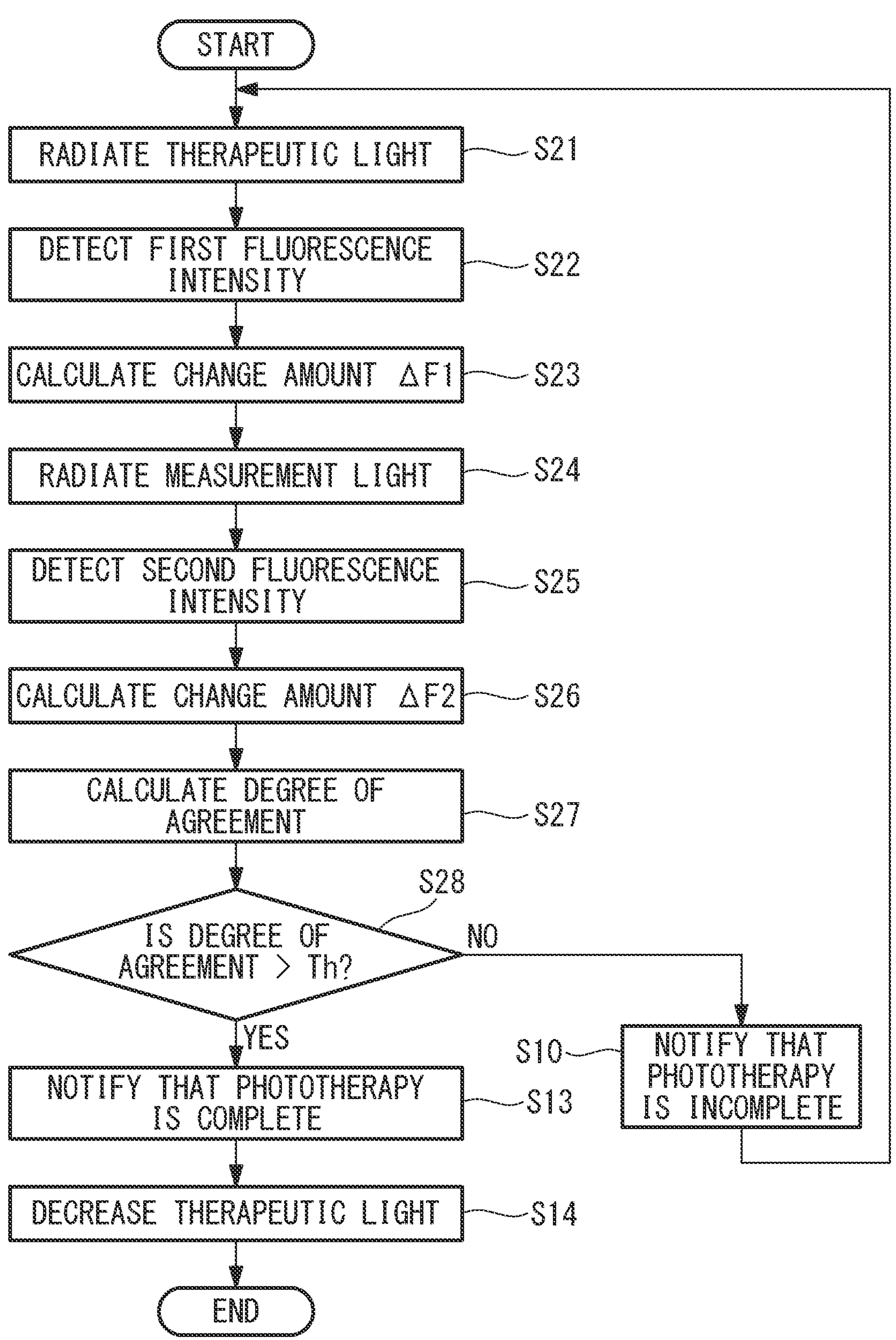
FIG. 9 is a flowchart showing the operations of the phototherapy progress measuring device and the phototherapy system in FIG. 7.

As with the first embodiment, a phototherapy progress measuring method shown in FIG. 9 is executed by the phototherapy progress measuring device 20 during phototherapy.

The phototherapy progress measuring method includes: step S21 for radiating the therapeutic light beam L2 onto the affected portion A; step S22 for detecting the first fluorescence intensity F1, which is the intensity of the fluorescence generated in the affected portion A due to the irradiation with the therapeutic light beam L2; step S24 for radiating the measurement light beam L3 onto the affected portion A; step S25 for detecting the second fluorescence intensity F2, which is the intensity of the fluorescence generated in the affected portion A due to the irradiation with the measurement light beam L3; steps S23, S26, and S27 for calculating the progress information by employing the fluorescence intensities F1 and F2; and step S28 for determining, on the basis of the progress information, whether the phototherapy of the affected portion A has been completed.

After starting the phototherapy, the therapeutic light beam L2 and the measurement light beam L3 are radiated onto the affected portion A in an alternating manner (steps S21 and S24) and the light detection portion 11 detects the first fluorescence intensity F1 and the second fluorescence intensity F2 in an alternating manner (steps S22 and S25). Then, the computation portion 14 calculates the change amount ΔF1 of the first fluorescence intensity F1 per unit time and the change amount ΔF2 of the second fluorescence intensity F2 per unit time (steps S23 and S26) and calculates, as the progress information, the degree of agreement between the change amount ΔF1 and the change amount ΔF2 (step S27).

Next, the determination portion 15 compares the degree of agreement with the prescribed threshold Th (step S28). In the case in which the degree of agreement is equal to or less than the threshold Th ("NO" in step S28), the determination portion 15 determines that the degree of agreement is equal to or less than the prescribed threshold Th and notifies the doctor about the determination result indicating the information (step S10). After it is determined that the degree of agreement is equal to or less than the threshold Th, steps S21 to S27 are repeated until it is determined that the degree of agreement has exceeded the threshold Th.

In the case in which the degree of agreement is greater than the threshold Th ("YES" in step S28), the determination portion 15 determines that the degree of agreement has exceeded the prescribed threshold Th and notifies the doctor about the determination result indicating the information (step S13), and the therapeutic-light adjustment portion 16 decreases the intensity of the therapeutic light beam L2 (step S14).

As has been described above, with this embodiment, the second fluorescence intensity F2 of the fluorescent agent that re-accumulates in the affected portion A during the phototherapy is acquired as the reference data. The change amount ΔF1 approaches the change amount ΔF2 with the phototherapy approaching the completion, and the degree of agreement between the change amount ΔF1 and the change amount ΔF2 represents the accurate progress of the phototherapy of the affected portion A. It is possible to calculate such a degree of agreement as the progress information, and it is possible to measure the accurate progress of the phototherapy. In addition, it is possible for the doctor to accurately determine whether the phototherapy has been completed on the basis of the progress information.

In addition, the degree of agreement is calculated, in real time, from the fluorescence intensities F1 and F2. Accordingly, it is possible to measure, in real time, the accurate progress of the phototherapy and it is possible for the doctor to determine, in real time, whether the phototherapy has been completed.

In this embodiment, the phototherapy progress measuring device 20 starts to measure the progress of the phototherapy simultaneously with the start of the phototherapy; however, alternatively, the phototherapy progress measurement may be started when the change amount ΔF1 takes a non-negative value for the first time, as with the first embodiment.

In other words, after starting the phototherapy, the computation portion 14 calculates the change amount ΔF1 each time the first fluorescence intensity F1 is detected. The therapeutic-light adjustment portion 16 causes the therapeutic light source 3 to output the therapeutic light beam L2 until the change amount ΔF1 takes a non-negative value for the first time since the start of the phototherapy and causes, after the change amount ΔF1 has taken a non-negative value for the first time, the therapeutic light source 3 to output the therapeutic light beam L2 and the measurement light beam L3 in an alternating manner.

With this configuration, because the therapeutic light beam L2 is continuously radiated onto the affected portion A until the change amount ΔF1 takes a negative value for the first time, it is possible to decrease the treatment time of the affected portion A.

In this embodiment, the therapeutic light beam L2 and the measurement light beam L3 are switched by changing the outputs of the therapeutic light source 3; however, alternatively, the light beams L2 and L3 may be switched by changing an irradiation distance for the therapeutic light beam L2 to reach the affected portion A. The irradiation distance is the distance from the distal end of the probe 4 from which the therapeutic light beam L2 is emitted to the affected portion A. For example, the irradiation distance is manually changed by the doctor by moving the probe 4 in the longitudinal direction in a reciprocating manner or is automatically changed by a motor (not shown) by moving the probe 4 in a reciprocating manner.

By increasing the irradiation distance, it is possible to decrease the intensity of the therapeutic light beam L2 radiated onto the affected portion A and to use the low-intensity therapeutic light beam L2 as the measurement light beam L3.

In addition, in this embodiment, a measurement light source that generates and outputs the measurement light beam L3 may be provided separately from the therapeutic light source 3.

In the above-described first and second embodiments, the display portion 6 may display the progress information in addition to or instead of the determination results of the determination portion 15. For example, the display portion 6 may display, as the progress information, the accumulated value I, the change amounts ΔF1 and ΔF2, and the numerical value of the degree of agreement and may display graphs showing temporal changes of these values.

In addition, the display portion 6 may display, as the progress information, displays indicating the progress of phototherapy of individual affected portions A on an endoscope image in a superimposed manner. With this configuration, it is possible for the doctor to easily ascertain the progress of the individual affected portions A on the basis of the displays added to the affected portions A in the endoscope image.

For example, "P1", "P2", "P3", or "P4" is added to each of the affected portions A in the endoscope image. "P1" indicates the stage in which the fluorescence intensity F is monotonically attenuating and the phototherapy is in progress. "P2" indicates the stage in which the temporal change of the fluorescence intensity F is substantially zero and the progress of the phototherapy has stopped. "P3" indicates the stage in which the fluorescence intensity F increases and the phototherapy and the re-accumulation of the fluorescent agent both are in progress. "P4" indicates the stage in which the progress of the phototherapy has stopped and only the re-accumulation of the fluorescent agent is in progress.

In the above-described first and second embodiments, the notification portion is the display portion 6 that displays the determination results of the determination portion 15; however, alternatively, the determination results may be notified by means of other means. For example, the notification portion may output sounds in accordance with the determination results.

In the above-described first and second embodiments, the phototherapy progress measuring devices 10 and 20 are part of the endoscope system; however, alternatively, the devices may be independent from the endoscope system. For example, the phototherapy progress measuring devices 10 and 20 may be separate devices from the endoscope processor 101, and the detection of the fluorescence Lf in the affected portion A and the irradiation of the affected portion A with the measurement light beam L3 may be performed via a probe disposed outside the endoscope 1.

In addition, the above-described embodiments have been described in terms of examples in which the reference data are data of the second fluorescence intensity, which is the intensity of the fluorescence generated by the fluorescent agent that re-accumulates in the affected portion during the phototherapy, or preset data that represent temporal changes of the intensity of the fluorescence generated by the fluorescent agent due to the irradiation with the therapeutic light beam, excluding the intensity of the fluorescence generated by the re-accumulating fluorescent agent; however, the reference data are not limited thereto, and other reference data may be employed, so long as data are based on fluorescence intensity associated with the fluorescent agent that is in the affected portion and is not involved in the phototherapy and are determined in association with fluorescence that could be involved in the fluorescence intensity due to the therapeutic light beam L2 in the final stage of the phototherapy and that is based on the fluorescent agent which is in the affected portion and is not involved in the phototherapy.

REFERENCE SIGNS LIST

100, 200 phototherapy system
20 phototherapy progress measuring device
3 therapeutic light source
4 probe (therapeutic-light irradiation portion)
6 display portion (notification portion)
8 image acquisition portion
11 light detection portion
12 intensity-data generation portion
13 storage portion
14 computation portion
15 determination portion
16 therapeutic-light adjustment portion
A affected portion
D1, D2, D3 preset data
F, F1 first fluorescence intensity
F2 second fluorescence intensity
ΔF, ΔF1, ΔF2 change amount
I accumulated value

The invention claimed is:

1. A phototherapy progress measuring method for measuring a progress of a phototherapy of an affected portion, a fluorescent agent being administered to the affected portion and comprising a pre-accumulated fraction accumulated in the affected portion prior to the phototherapy and a re-accumulated fraction not accumulated in the affected portion prior to the phototherapy and re-accumulated in the affected portion during the phototherapy, the method comprising:

radiating a therapeutic light beam onto the affected portion from a therapeutic light source, the therapeutic light beam being used for treating the affected portion by exciting the fluorescent agent;

detecting, by a photodetector, a first fluorescence intensity, which is an intensity of fluorescence generated as a result of exciting the fluorescent agent; and calculating, by employing the first fluorescence intensity and reference data, progress information representing the progress of the phototherapy of the affected portion, wherein the reference data is:

data of a second fluorescence intensity, which is an intensity of fluorescence in the re-accumulated fraction of the fluorescent agent; or preset data that is prepared and stored in a memory prior to the phototherapy and that represents a temporal change of an intensity of fluorescence of the fluorescent agent due to an irradiation of the therapeutic light beam, excluding the intensity of fluorescence in the re-accumulated fraction of the fluorescent agent.

2. The phototherapy progress measuring method according to claim 1, further comprising storing the first fluorescence intensity in a time sequence and generating intensity data representing a temporal change of the first fluorescence intensity, wherein calculating the progress information includes:

selecting, from among a plurality of the preset data, one preset data that is most similar to the intensity data so as to serve as the reference data;

calculating, by employing the selected preset data, a corrected change amount of the first fluorescence intensity per unit time; and calculating, by employing the corrected change amount, an accumulated value of the change amount of the first fluorescence intensity per unit time, and wherein the accumulated value serves as the progress information.

3. The phototherapy progress measuring method according to claim 1, further comprising:

radiating a measurement light beam that is weaker than the therapeutic light beam onto the affected portion; and detecting the second fluorescence intensity, which is an intensity of fluorescence generated as a result of radiating the measurement light beam onto the affected portion, wherein calculating the progress information comprises:

calculating a degree of agreement between a change amount of the first fluorescence intensity per unit time and a change amount of the second fluorescence intensity per unit time, and wherein the degree of agreement serves as the progress information.

4. The phototherapy progress measuring method according to claim 3, wherein radiating the measurement light beam includes switching an intensity of the therapeutic light beam radiated onto the affected portion from a first intensity to a second intensity that is lower than the first intensity, and the measurement light beam is the therapeutic light beam in which the intensity thereof is decreased to the second intensity.

5. The phototherapy progress measuring method according to claim 4, wherein the intensity of the therapeutic light beam radiated onto the affected portion is switched between the first intensity and the second intensity by changing outputs of a therapeutic light source that outputs the therapeutic light beam.

6. The phototherapy progress measuring method according to claim 4, wherein the intensity of the therapeutic light beam radiated onto the affected portion is switched between the first intensity and the second intensity by changing an irradiation distance for the therapeutic light beam to reach the affected portion.

7. The phototherapy progress measuring method according to claim 1, further comprising determining whether a change amount of the first fluorescence intensity per unit time is negative, wherein the progress information is calculated after it is determined that the change amount is not negative.

8. The phototherapy progress measuring method according to claim 1, further comprising determining, on the basis of the progress information, whether the phototherapy of the affected portion has been completed.

9. A processor that measures a progress of a phototherapy of an affected portion, a fluorescent agent being administered to the affected portion and comprising a pre-accumulated fraction accumulated in the affected portion prior to the phototherapy and a re-accumulated fraction not accumulated in the affected portion prior to the phototherapy and re-accumulated in the affected portion during the phototherapy, the processor being configured to:

control a therapeutic light source to radiate a therapeutic light beam onto the affected portion, the therapeutic light beam being used for treating the affected portion by exciting the fluorescent agent;

control a photodetector to detect a first fluorescence intensity, which is an intensity of fluorescence generated as a result of exciting the fluorescent agent; and calculate, by employing the first fluorescence intensity and reference data, progress information representing the progress of the phototherapy of the affected portion, wherein the reference data is:

data of a second fluorescence intensity, which is an intensity of fluorescence in the re-accumulated fraction of the fluorescent agent; or preset data that is prepared and stored in a memory prior to the phototherapy and that represents a temporal change of an intensity of fluorescence of the fluorescent agent due to an irradiation of the therapeutic light beam, excluding the intensity of fluorescence in the re-accumulated fraction of the fluorescent agent.

10. The processor according to claim 9, wherein the processor is further configured to:

store the first fluorescence intensity in a time sequence and generate intensity data representing a temporal change of the first fluorescence intensity; and receive a plurality of the preset data from the memory;

select, from among the plurality of the preset data, one preset data that is most similar to the intensity data so as to serve as the reference data;

correct, by employing the selected preset data, a corrected change amount of the first fluorescence intensity per unit time; and calculate, by employing the corrected change amount, an accumulated value of the change amount of the first fluorescence intensity per unit time, wherein the accumulated value serves as the progress information.

11. The processor according to claim 9, wherein:

the photodetector is further configured to detect the second fluorescence intensity, which is an intensity of fluorescence generated as a result of radiating a measurement light beam that is weaker than the therapeutic light beam onto the affected portion, and the processor is further configured to calculate a degree of agreement between a change amount of the first fluorescence intensity per unit time and a change amount of the second fluorescence intensity per unit time, wherein the degree of agreement serves as the progress information.

12. The processor according to claim 11, wherein the processor is further configured to:

switch the intensity of the therapeutic light beam radiated onto the affected portion between a first intensity and a second intensity that is lower than the first intensity, wherein the measurement light beam is the therapeutic light beam in which the intensity thereof is decreased to the second intensity.

13. The processor according to claim 9, wherein the processor is further configured to:

determine whether a change amount of the first fluorescence intensity per unit time is negative; and calculate the progress information after it is determined that the change amount is not negative.

14. The processor according to claim 9, the processor is further configured to determine, on the basis of the progress information, whether the phototherapy of the affected portion has been completed.

15. A phototherapy system that performs a phototherapy of an affected portion by means of a fluorescent agent by radiating a therapeutic light beam onto the affected portion, the system comprising:

the therapeutic light source configured to output the therapeutic light beam;

a probe configured to radiate the therapeutic light beam onto the affected portion; and the processor according to claim 14, wherein the processor is further configured to output determination results.

16. The phototherapy system according to claim 15, wherein the processor is further configured to:

in a case in which the processor determines that the phototherapy of the affected portion has been completed, decrease the intensity of the therapeutic light beam.

17. The phototherapy system according to claim 15, further comprising:

an image acquisition portion comprising an imaging element and configured to acquire an image of the affected portion; and a display configured to display the image acquired by the image acquisition portion, wherein the display is configured to display the progress information.

18. The phototherapy system according to claim 17, wherein the display is further configured to display the progress information on the affected portion in the image in a superimposed manner.

* * * * *